United States Patent

Kalopissis et al.

[11] 3,984,402
[45] Oct. 5, 1976

[54] INDOANILINES FOR DYEING KERATINOUS FIBERS

[75] Inventors: Gregoire Kalopissis, Paris; Andree Bugaut, Boulogne-sur-Seine; Francoise Estradier, Paris, all of France

[73] Assignee: L'Oreal, Paris, France

[22] Filed: Dec. 24, 1974

[21] Appl. No.: 536,292

Related U.S. Application Data

[62] Division of Ser. No. 213,750, Dec. 29, 1971, Pat. No. 3,867,094.

[30] Foreign Application Priority Data

Dec. 30, 1970  Luxemburg............................ 62348
May 10, 1971  Luxemburg............................ 63144

[52] U.S. Cl................................. 260/244 R; 8/10; 8/10.1; 8/10.2; 8/11; 260/270 R; 260/293.77; 260/293.79; 260/326.11 R; 260/396 N; 424/47; 424/71; 424/DIG. 1; 424/DIG. 2

[51] Int. Cl.².............. C07C 119/14; C07D 265/36

[58] Field of Search... 260/396 N, 244 R, 326.11 R, 260/293.79, 293.77; 8/10, 10.1

[56] References Cited

OTHER PUBLICATIONS

Chem. Abstracts, 24:3944.
Chem. Abstracts, 41:2901f (1947).

*Primary Examiner*—Vivian Garner
*Attorney, Agent, or Firm*—Cushman, Darby & Cushman

[57] ABSTRACT

Indoaniline having the formula

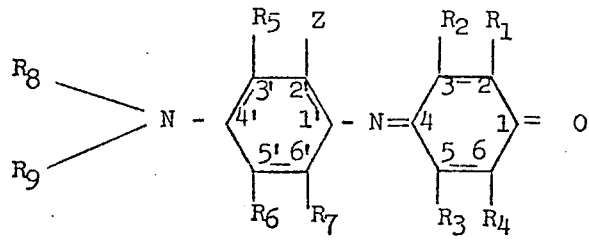

wherein $R_1$, $R_2$, $R_3$ and $R_4$ each independently represent a member selected from the group consisting of hydrogen, lower alkyl or halogen with 1 – 2 of these substituents being other than hydrogen; $R_5$, $R_6$ and $R_7$ each independently represent a member selected from the group consisting of hydrogen, lower alkyl and lower alkoxy; $R_8$ and $R_9$ each independently represent a member selected from the group consisting of hydrogen, lower alkyl and lower alkyl substituted with a member selected from the group consisting of amino, hydroxy, carbamoyl, piperidinyl and acylamino, $R_8$ and $R_5$ or $R_9$ and $R_6$ being able to form with the adjacent nitrogen atom a dihydro-oxazine or pyrroline heterocycle; Z represents a member selected from the group consisting of amino, acylamino and hydroxy, and the salts formed by these indoanilines with organic or inorganic acids, in particular, their acetates, oxalates, hydrochlorides, hydrobromides, persulfates, perchlorates and the double zinc salts of these compounds, which can, of course, be in a tautomeric form of that represented by the above formula. These indoanilines are usefully employed for dyeing keratinous fibers, and, in particular, human hair.

2 Claims, No Drawings

INDOANILINES FOR DYEING KERATINOUS FIBERS

This is a division of application Ser. No. 213,750 filed Dec. 29, 1971, now U.S. Pat. No. 3,867,094.

The present invention relates to novel indoanilines having the formula

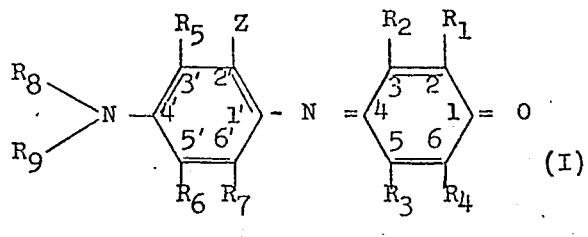

(I)

wherein $R_1$, $R_2$, $R_3$ and $R_4$ each independently represents a member selected from the group consisting of hydrogen, lower alkyl having 1 – 6 carbon atoms and halogen such as chlorine and bromine with the proviso that 1 – 2 of $R_1$, $R_2$, $R_3$ and $R_4$ are other than hydrogen; $R_5$, $R_6$ and $R_7$ each independently represent a member selected from the group consisting of lower alkyl having 1 – 6 carbon atoms and lower alkoxy having 1 – 6 carbon atoms; $R_8$ represents a member selected from the group consisting of hydrogen, lower alkyl having 1 – 6 carbon atoms, lower alkyl having 1 – 6 carbon atoms and substituted with a member selected from the group consisting of amino, hydroxyl, carbamoyl, piperidinyl and acylamino and together with $R_5$ and the nitrogen atom to which $R_8$ is attached form a heterocycle selected from the group consisting of dihydro-oxazine and pyrroline; $R_9$ represents a member selected from the group consisting of hydrogen, lower alkyl having 1 – 6 carbon atoms, lower alkyl having 1 – 6 carbon atoms and substituted with a member selected from the group consisting of amino, hydroxyl, carbamoyl, piperidinyl and acylamino, and together with $R_6$ and the nitrogen atom to which $R_9$ is attached form a heterocycle selected from the group consisting of dihydro-oxazine and pyrroline; Z represents a member selected from the group consisting of an amino, acylamino and hydroxy; and the salts formed by these indoanilines with organic or inorganic acids, and the double zinc salts of these compounds, which can, of course, be in a tautomeric form of that represented by formula I.

The organic or inorganic acid salts of the compounds of formula I can be acetates, oxalates, hydrochlorides, hydrobromides, persulfates or perchlorates.

The indoanilines or indoaniline salts of formula I can be prepared by four different processes described below.

METHOD 1

A first process of obtaining the indoanilines of formula I or their salts comprises reacting a paraaminophenol having the formula:

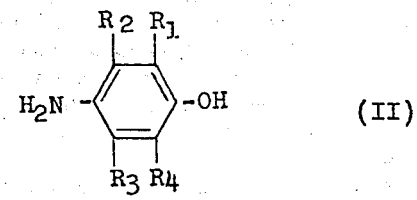

(II)

wherein $R_1$, $R_2$, $R_3$ and $R_4$ have the meaning given above, or alternatively, a salt of such a compound, for example, the hydrochloride, hydrobromide or sulfate thereof, with a compound having the formula

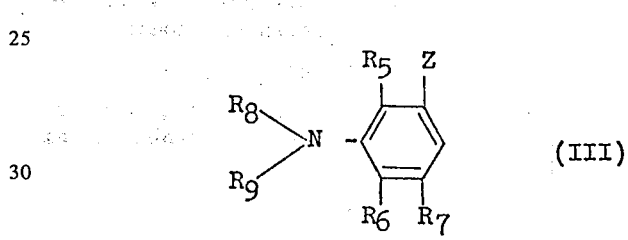

(III)

wherein $R_5$, $R_6$, $R_7$, $R_8$, and Z have the meaining above, or alternatively with a salt of such a compound, for example, the dihydrochloride, dihydrobromide or sulfate thereof.

The reaction can be performed in an aqueous medium, an aqueous alcoholic medium or an aqueous acetonic medium, at a pH made alkaline by addition to said chosen medium of an aqueous solution of sodium, potassium or ammonium hydroxide, the pH preferably ranging from about 8 to 10 at a temperature between —5° C and 40°C and in the presence of an oxidizing agent such as air, hydrogen peroxide, ammonium persulfate or potassium ferricyanide. The indoaniline of formula I is then isolated in the form of a free base. When an aqueous alcoholic medium is employed the alcohol can be present in amounts of about 20 to 50 percent by weight of said medium and the alcohol employed is generally a lower alkanol having 1 – 4 carbon atoms.

When an aqueous acetonic medium is employed, acetone can comprise between about 10 to 30 weight percent of the medium.

The amount of oxidizing agent used can vary between about 1 to 5 times the stoichiometric quantity for oxidising the paraaminophenol to the corresponding quinone-imine. This amount is preferably 1-3 moles of persulphate or 2-5 moles of ferricyanide for 1 mole of paraaminophenol.

The reaction can also be performed in an aqueous medium between 0° and 20°C at an acid pH, preferably ranging from about 1 to 5, and in the presence of a ferric chloride solution present in amounts of about 2 to 6 moles per mole of paraamino phenol. The indoaniline of formula I is then isolated in the hydrochloride form.

Representative paraaminophenols of formula II that can be used in accordance with the present invention are, 3-methyl 4-amino phenol, 2,5-dimethyl 4-amino phenol, 3,5-dimethyl 4-amino phenol, 2,3-dimethyl 4-amino phenol, 2-methyl 4-amino phenol, 2,6-dimethyl 4-amino phenol, 2,6di-tert, -butyl 4-amino phenol 2-chloro-4-amino phenol and 3-chloro 4-amino phenol.

Compounds representative of those of formula III include metaphenylenediamine, metatoluylenediamine, 2,4-diamino anisole, 3,5-diamino toluene, 1,3-dimethyl-2,4-diamino benzene, N,N-dimethyl metaphenylenediamine, 6-hydroxy phenomorpholine, 6-hydroxy-4-methyl phenomorpholine, 3-acetylamino N,N-dimethylaniline, 2-methyl-5-acetylamino aniline, 6-amino phenomorpholine, and 1-ethyl-6-amino indoline.

Generally, the paraaminophenol represented by formula II and the compound represented by formula III are employed in essentially equimolar amounts.

METHOD 2

The indoanilines of formula I can also be prepared by condensation of a benzoquinonemonoimine having formula

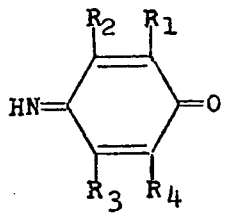

(IV)

wherein $R_1$, $R_2$, $R_3$ and $R_4$ have the meaning given above, on a compound of formula III above, this condensation taking place at ambient temperature, either in an aqueous medium or in an aqueous alcoholic medium as defined above or in a solvent such as methylisobutylketone or dioxane. Essentially, equimolar amounts of the benzoquinonemonoimine and compound III are employed.

METHOD 3

The indoanilines of formula I can also be prepared by condensation of a quinone-chloroimide having the formula

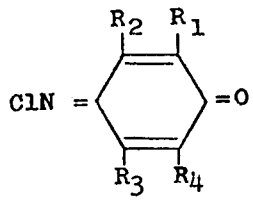

(V)

wherein $R_1$, $R_2$, $R_3$ and $R_4$ have the meaning give above, on compound of formula III, this condensation being performed in an aqueous medium, an aqueous alcoholic medium or an aqueous acetonic medium, also as defined above, at a temperature between 0° and 40°C.

Representative quinone-chloroimides that can be used include, for example, 3-methyl quinone chloroimide, 2-chloro quinone chlorimide, 3-chloro quinone chloroimide, 2,5-dimethyl quinone chloroimide, 2,3-dimethyl quinone chlorimide and 3,5-dimethyl quinone chloroimide. Essentially equimolar amounts of the quinone-chloroimide and compound III are employed.

METHOD 4

The indoanilines of formula I can also be prepared by reacting a nitroso derivative having the formula

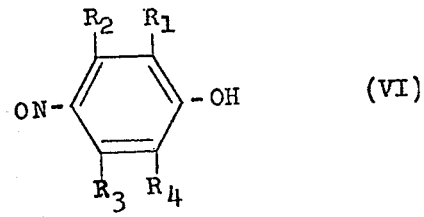

wherein $R_1$, $R_2$, $R_3$ and $R_4$ have the meaning above, with a compound of formula III. The condensation reaction is performed in an alcohol medium in the presence of zinc chloride at the reflux temperature of the reaction medium. salt. The alcohol used for the reaction medium can be a lower alkanol having 1 – 4 carbon atoms and the zinc chloride is generally present in amounts sufficient for precipitating the product.

The indoanilines according to the present invention and their salts constitute dyes which present good dyeing power with regard to keratinous fibers and, in particular, human hair, this in a pH range varying from 4 to 11. Because of their great affinity for these fibers they can be used at very slight concentrations, for instance, from about 0.002 to 0.005% by weight of the dye composition, which explains why even salts that are only slightly soluble in water can be effectively used.

The indoanilines of the present invention make it possible to obtain a very wide range of shades, in particular violets, blues, greens, roses, silver grays and ash blonds which present exceptional qualities of brilliance and richness in glints. After dyeing, the hair presents a pearly and iridescent appearance.

Consequently, the present invention also provides a novel dyeing composition for keratinous fibers, in particular human hair, characterized by the fact that it contains in solution at least a compound of formula I or a salt of this compound.

The dye compositions according to the invention can contain only the compounds of formula I, in which case they make it possible to obtain the entire range of shades, with the exception of the yellows, and with application times that can be extremely short, of the order of 3 minutes at ambient temperature, beacuse of the great affinity of the indoanilines of formula I with regard to keratinous fibers.

The compositions according to the invention can also contain other direct dyes, for example, anthraquinone dyes, nitro dyes of the benzene series, indamines, indophenols, oxazines, azines or indoanilines other than those of formula I.

Because of the great dyeing power of the novel compounds of formula I, their concentration in the compositions according to the invention can, as has been said above, be extremely slight, of the order of 0.002% by weight. However, this concentration can vary from 0.002 to 2% and preferably between about 0.005 and 0.5% by weight.

The dye compositions according to the present invention are in the form of aqueous solutions, to which most often have been added lower molecular weight alcohols such as ethanol or isopropanol, or glycols such as propyleneglycol or butylglycol, the alcohol or glycol facilitating the solution of the dye in the composition. The proportion of alcohol used is generally between 20 and 70% by weight, while the proportion of glycol is generally between 1 and 6% by weight.

The compositions according to the invention can also contain various ingredients usually used in capillary cosmetics, for example, wetting agents, dispersing agents, swelling agents, penetrating agents, thickeners, softeners or perfumes. They can also be packaged under pressure in aerosol bombs or containers, together with a conventional aerosol propellant such as dichlorodifluoromethane, trichloromonofluoromethane and their mixtures. Obviously other conventional aersol propellants can be used.

The pH of the dye compositions according to the invention can vary between 4 to 11. Preferably, however, the pH ranges between 5 and 9. To relate this pH at a desired value, it is possible to use as alkalizing agents ammonia or an amine such as mono- or di- or triethanolamine and as acidifying agents, acetic acid or lactic acid.

Dyeing of keratinous fibers, in particular, human hair, with the dye compositions according to the invention, can be performed in the usual way, by application of the composition to the fibers to be dyed, the composition being left in contact with the fibers for a time varying from 3 to 30 minutes. Following this application, the fibers are rinsed and, if desired, washed. Thereafter, the thus treated fibers are dried.

In another embodiment of the present invention, the novel indoanilines can be employed in the production of capilliary hair-setting lotions. These lotions comprise an aqueous alcohol solution, at least one cosmetic resin and at least one indoaniline of formula I or a salt thereof. The amount of indoaniline or its salt present in the hair-setting lotion according to this invention can be extremely slight. Such an amount generally varies between 0.002 and 1% by weight and preferably between 0.002 and 0.5% by weight, of the total hair-setting lotion composition, the pH of which generally lies between 5 – 8.

Representative cosmetic resins that can be employed in the hair-setting lotions of the present invention include, for instance, polyvinylpyrrolidone having a molecular weight of 40,000 – 400,000, copolymer of crotonic acid and vinyl acetate, said copolymer having a molecular weight ranging from about 10,000 to 70,000, copolymer vinylpyrrolidone and vinyl acetate, wherein the ratio of PVP to VA ranges between 50 – 70: 50 – 30, said copolymer having a molecular weight ranging from about 30,000 to 200,000 and maleic anhydride - butylvinyl ether copolymers, a 1% solution of which in methylethyl ketone has a viscosity of 0.1–3.5 cps at 25° C. These resins are used in a proportion of 1 to 3% by weight of the hair-setting lotion composition.

The alcohols suitable for the preparation of the hair-setting lotions according to the invention are low molecular weight alkanols, such as ethanol or isopropanol which are present in amounts of about 20 to 70% by weight of the total hair-setting lotion composition.

The setting lotion of the present invention can contain only the indoanilines of formula I, in which case they constitute shading compositions which make it possible to give the hair extremely luminous glints and a pearly or iridescent appearance.

However, the hair-setting lotions of this invention can also contain other direct dyes, for example, anthraquinone dyes, nitro dyes of the benzene series, indamines, indophenols, oxazines, azines or indoanilines other than those of formula I.

The hair-setting lotions according to the invention are usually used by application to wet hair, previously washed and rinsed, followed by rolling the hair up on curlers and drying the hair.

The following examples are intended to illustrate the various aspects of the present invention. Unless otherwise specified, all parts and percentages are by weight and all temperatures are expressed in degrees centigrade.

EXAMPLE 1

N-[(2',4'-diamino) phenyl]-3-methyl benzoquinone imine having the below formula is prepared as follows.

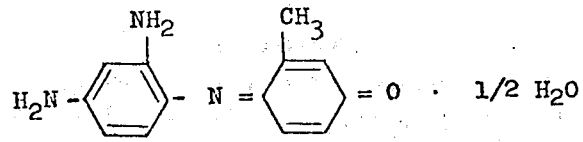

To a solution, cooled by an ice-salt mixture, of 0.02 mole (4.08 g) of 3-methyl 4-amino phenol hydrobromide and 0.02 mole (3.62 g) of metaphenylenediamine dihydrochloride in 120 cc of water, there is added 0.02 mole (4.6 g) of ammonium persulfate to which have been added 25 cc of ammonia at 22° Be. The reaction mixture is allowed to stand for 15 minutes at 0° C. The above indoaniline is filtered and washed with water. After recrystallization in a dimethylformamide-water mixture and drying under vacuum, the product melts at 147° C.

Molecular weight calculated for $C_{13}H_{13}N_3O \cdot \frac{1}{2} H_2O = 236$

Molecular weight found by potentiometric determination in dimethylformamide with 0.1N tetra-n-butylammonium hydroxide in solution in a mixture of isopropanol and methanol = 234.

| Analysis | Calculated for | Found | |
|---|---|---|---|
| | $C_{13}H_{13}N_3O \cdot \frac{1}{2} H_2O$ | | |
| C% | 66.10 | 66.26 | 66.31 |
| H% | 5.93 | 6.01 | 5.91 |
| N% | 17.78 | 17.48 | 17.39 |

EXAMPLE 2

N-[(2', 4'-diamino-3',5'-dimethyl) phenyl]-3-methyl benzoquinone imine is prepared as follows

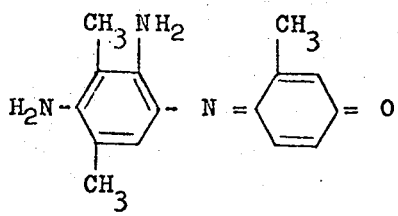

There are dissolved, on the one hand, 0.01 mole (1.55 g) of 3-methyl quinone chloroimide in 25 cc of 96° ethanol and, on the other hand, 0.01 mole (2.09 g) of 1,3-dimethyl-2,4-diamino benzene in 25 cc of water to which have been added 10 cc of ammonia at 22° Be and 1 cc of a normal soda solution. The two solutions, previously cooled, are mixed and the reaction mixture is allowed to stand for 20 minutes at 0° C. The above indoaniline precipitates in the form of green crystals with golden glints. It is filtered, washed with ethyl alcohol and then with water. After vacuum drying, the product is chromatographically pure and melts at 170° C.

Molecular weight calculated for $C_{15}H_{17}N_3O = 255$

Molecular weight found by potentiometric determination in acetic acid by perchloric acid = 258.

| Analysis | Calculated for | Found | |
|---|---|---|---|
| | $C_{15}H_{17}N_3O$ | | |
| C% | 70.59 | 70.49 | 70.42 |
| H% | 6.66 | 6.77 | 6.58 |
| N% | 16.47 | 16.28 | 16.26 |

EXAMPLE 3

N-[(3',5'-dimethyl-2',4'-diamino) phenyl]-3,5-dimethyl benzoquinone imine, having the below formula, is prepared as follows:

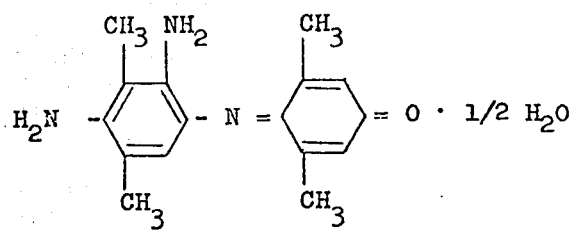

To a solution, cooled to 0°C, of 0.01 mole (1.37 g) of 3,5-dimethyl-4-amino phenol and 0.01 mole (2.09 g) of 1,3-dimethyl-2,4-diamino benzene dihydrochloride in 100 cc of an 0.5N soda solution there is added 0.01 mole (2.3g) of ammonium persulfate in 50 cc of water. The reaction mixture is allowed to stand for 15 minutes at 0° C. The above indoaniline precipitates and is filtered therefrom, after which it is washed with water.

After vacuum drying, the product melts at 195° C. It is chromatographically pure.

Molecular weight calculated for

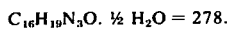

Molecular weight found by potentiometric determination in acetic acid by perchloric acid = 275.

| Analysis | Calculated for | Found | |
|---|---|---|---|
| | $C_{16}H_{19}N_3O \cdot \frac{1}{2} H_2O$ | | |
| C% | 69.06 | 68.84 | 68.76 |
| H% | 7.19 | 7.12 | 7.09 |
| N% | 15.10 | 14.81 | 14.93 |

EXAMPLE 4

N-[(3',5'-dimethyl-2',4'-diamino) phenyl]-2,3-dimethyl benzoquinone imine, having the below formula, is prepared as follows:

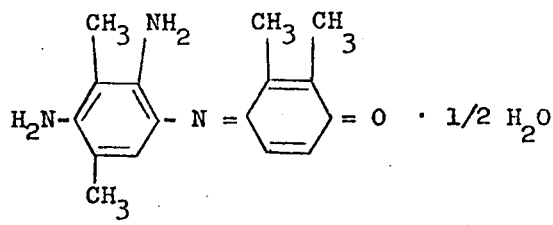

There are dissolved, on the one hand, 0.02 mole (3.4 g) of 2,3-dimethyl quinonechloroimide in 50 cc of ethyl alcohol and, on the other hand, 0.02 mole (4.18 g) of 1,3-dimethyl-2,4-diamino benzene dihydrochloride in 80 cc of water to which have been added 10 cc of ammonia at 22° Be and 5 cc of a normal soda solution. The two solutions, previously cooled, are mixed and the reaction mixture is allowed to stand for an hour at ambient temperature, after which 100 cc of ice water are added. Then 2.21 g of the above indoaniline are filtered which, after washing with water and vacuum drying, is chromatographically pure and melts at 206°C.

Molecular weight calculated for

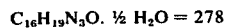

Molecular weight found by potentiometric determination in acetic acid by perchloric acid = 284.

| Analysis | Calculated for | Found | |
|---|---|---|---|
| | $C_{16}H_{19}N_3O \cdot \frac{1}{2} H_2O$ | | |
| C% | 69.06 | 68.69 | 68.96 |
| H% | 7.19 | 7.03 | 7.12 |
| N% | 15.10 | 15.00 | 15.11 |

EXAMPLE 5

N-[(2',4'-diamino) phenyl]-2,5-dimethyl benzoquinone imine, having the below formula, is prepared as follows:

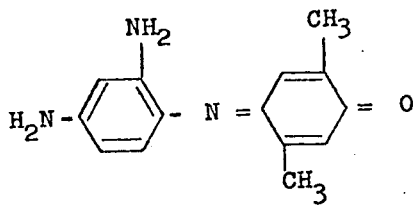

To a solution, cooled by an ice-salt mixture, of 0.02 mole (2.74 g) of 2,5-dimethyl-4-amino phenol and 0.02 mole (3.62 g) of metaphenylenediamine dihydrochloride in 120 cc of 1.75 N soda solution there is added 0.02 mole (4.6 g) of ammonium persulfate in 50 cc of water to which have been added 15 cc of ammonia at 22° Be. The reaction mixture is allowed to stand for 45 minutes at 0° C. The above indoaniline in crystal form is then filtered from the reaction mass and washed with water. After recrystallization in a dimethylformamide-water mixture and vacuum drying, the product melts at 173° C.

Molecular weight calculated for $C_{14}H_{15}N_3O = 241$

Molecular weight found by potentiometric determination in acetic acid by perchloric acid = 243.

| Analysis | Calculated for | Found | |
|---|---|---|---|
| | $C_{14}H_{15}N_3O$ | | |
| C% | 69.70 | 69.21 | 69.34 |
| H% | 6.22 | 6.18 | 6.25 |
| N% | 17.42 | 17.24 | 17.17 |

EXAMPLE 6

N-[(3',5'-dimethyl-2',4'-diamino) phenyl]-2,5-dimethyl benzoquinone imine, having the below formula, is prepared in accordance with method 1, as follows:

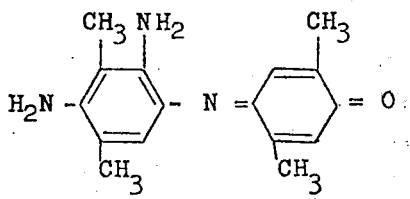

To a solution of 0.015 mole (3.13 g) of 1,3-dimethyl-2,4-diamino benzene dihydrochloride in 50 cc of ice water there are quickly added, first, 0.01 mole (2.3 g) of ammonium persulfate in 50 cc of ice water to which have been added 6 cc of ammonia at 22° Be, then, immediately afterward, 0.01 mole (1.37 g) of 2,5-dimethyl 4-amino phenol dissolved in 40 cc of 4N soda solution. The reaction mixture is allowed to stand for 10 minutes at 0° C. The above indoaniline is filtered therefrom, washed with water and, after recrystallization in acetone, is in the form of green crystals with metallic glints and exhibiting a melting point of 207° C.

Molecular weight calculated for $C_{16}H_{19}N_3O = 269$

Molecular weight found by potentiometric determination in acetic acid by perchloric acid = 268.

| Analysis | Calculated for | Found | |
|---|---|---|---|
| | $C_{16}H_{19}N_3O$ | | |
| C% | 71.37 | 71.22 | 71.40 |
| H% | 7.06 | 7.24 | 7.21 |
| N% | 15.61 | 15.90 | 15.76 |

EXAMPLE 7

N-[(3',5'-dimethyl-2',4'-diamino) phenyl]-2,5-dimethyl benzoquinone imine is prepared in accordance with method 2 as follows:

On the one hand, 0.01 mole (1.7 g) of 2,5-dimethyl quinonechloroimide is dissolved in 50 cc of 96° ethanol and, on the other hand, 0.01 mole (2.09 g) of 1,3-dimethyl-2,4-diamino benzene is dissolved in 25 cc of water to which have been added 10 cc of ammonia at 22° Be and 1 cc of normal soda solution. The two solutions, previously cooled, re mixed and the reaction mixture is allowed to stand for 30 minutes at 0° C. The above indoaniline precipitates in the form of green crystals with metallic glints. It is filtered, washed with ethyl alcohol and then with water. The product, after vacuum drying, melts at 206° C and does not show any drop in its melting point when mixed with the indoaniline prepared according to example 6.

EXAMPLE 8

N-[(2',4'-diamino) phenyl]-2-chloro benzoquinone imine, having the below formula, is prepared as follows:

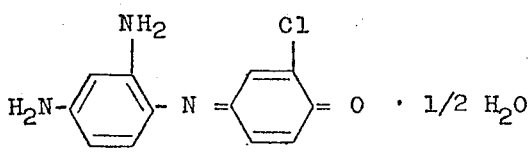

0.04 mole (7.20 g) of 2-chloro-4-amino phenol hydrochloride and 0.04 mole (7.24 g) of metaphenylenediamine dihydrochloride are dissolved in 200 cc of water. To this solution, cooled to 0° C, there is added little by little, with stirring, 0.04 mole (9.20 g) of ammonium persulfate dissolved in 100 cc of ice water to which have been added 50 cc of ammonia at 22° Be. The above indoaniline precipitates immediately in the form of green crystals. The product is filtered, washed with water to eliminate traces of metaphenylenediamine and after vacuum drying, the indoaniline chromatographically pure and melts at 189° C.

Molecular weight calculated for $C_{12}H_{10}N_3OCl \cdot \frac{1}{2} H_2O = 256.5$ Molecular weight found by potentiometric determination in acetic acid by perchloric acid = 254.

| Analysis | Calculated for | Found | |
|---|---|---|---|
| | $C_{12}H_{10}N_3OCl \cdot \frac{1}{2} H_2O$ | | |
| C% | 56.14 | 55.91 | 55.84 |
| H% | 4.67 | 4.59 | 4.61 |
| N% | 16.37 | 16.54 | 16.43 |
| Cl% | 13.84 | 13.61 | 13.78 |

EXAMPLE 9

N-[(2',4'-diamino-5'-methoxy) phenyl]-2-chloro benzoquinone imine, having the below formula, is prepared as follows:

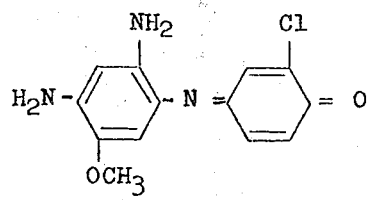

A solution is prepared by dissolving 0.02 mole (3.60 g) of 2-chloro 4-amino phenol hydrochloride in 50 cc of water. To this solution, cooled in an ice bath, there are added simultaneously, with stirring, with the aid of two dropping funnels, on the one hand, 0.02 mole (4.22 g) of 2,4-diamino anisole dihydrochloride dissolved in 50 cc of water, and, on the other hand, 0.02 mole (4.60 g) of ammonium persulfate dissolved in 50 cc of ice water to which have been added 50 cc of ammonia at 22° Be. The reaction mixture is allowed to stand for 15 minutes at 0° C. The above indoaniline precipitates in crystallized form and is filtered therefrom, after which it is washed with water and vacuum dried. The product is chromatographically pure and melts at 197° C.

Molecular weight calculated for $C_{13}H_{12}N_3O_2Cl$ = 277.5

Molecular weight found by potentiometric determination in acetic acid by perchloric acid = 272.

| Analysis | Calculated for | Found | |
|---|---|---|---|
| | $C_{13}H_{12}N_3O_2Cl$ | | |
| C% | 56.22 | 56.15 | 56.08 |
| H% | 4.32 | 4.46 | 4.38 |
| N% | 15.13 | 15.00 | 14.98 |
| Cl% | 12.79 | 12.66 | 12.61 |

EXAMPLE 10

N-[(2',4'-diamino-5'-methyl) phenyl]-2-chloro benzoquinone imine having the below formula is prepared as follows:

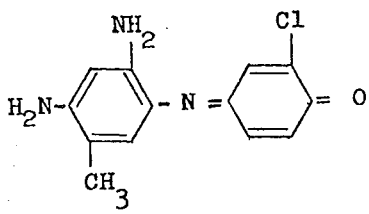

There are dissolved 0.02 mole (3.6 g) of 2-chloro 4-amino phenol hydrochloride and 0.02 mole (2.44 g) 2,4-diamino toluene in 100 cc of water. To this solution, cooled to 0°C, there is added little by little, with stirring, 0.02 mole (4.6 g) of ammonium persulfate dissolved in 50 cc of water to which have been added 25 cc of ammonia at 22° Be. The above inodaniline precipitates immediately in the form of mordore crystals.

The product is filtered washed with water and then with isopropanol. After vacuum drying it is chromatographically pure and melts at 211° C.

Molecular weight calculated for $C_{13}H_{12}N_3OCl$ = 261.5

Molecular weight found by potentiometric determination in dimethylformamide with 0.1N tetra-n-butylammonium hydroxide in solution in a mixture of isopropanol and methanol = 259.

| Analysis | Calculated for | Found | |
|---|---|---|---|
| | $C_{13}H_{12}N_3OCl$ | | |
| C% | 59.65 | 59.43 | 59.37 |
| H% | 4.59 | 4.67 | 4.52 |
| N% | 16.06 | 15.88 | 15.93 |
| Cl% | 13.57 | 13.48 | 13.52 |

EXAMPLE 11

N-[(3',5'-dimethyl-2',4'-diamino) phenyl]-2-chloro benzoquinone imine having the below formula is prepared as follows:

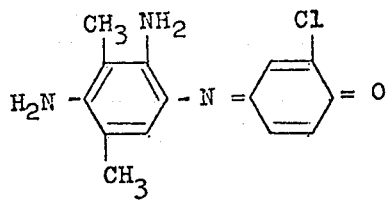

There are dissolved 0.04 mole (7.20 g) of 2-chloro 4-amino phenol hydrochloride and 0.04 mole (8.36 g) 1,3-dimethyl-2,4-diamino benzene dihydrochloride in 200 cc of water. To this solution, cooled to 0° C, there is added little by little, with stirring, 0.04 mole (9.20 g) of ammonium persulfate dissolved in 100 cc of water to which have been added 50 cc of ammonia at 22° Be. The reaction mixture is allowed to stand for one hour at 0° C. The above indoaniline, which has precipitated in the form of green crystals, is filtered. The product, after washing with water and vacuum drying, is chromatographically pure and melts at 157° C.

Molecular weight calculated for $C_{14}H_{14}N_3ClO$ = 275.5

Molecular weight found by potentiometric determination in acetic acid by perchloric acid = 278.

| Analysis | Calculated for | Found | |
|---|---|---|---|
| | $C_{14}H_{14}N_3ClO$ | | |
| C% | 60.98 | 60.78 | 61.14 |
| H% | 5.08 | 5.05 | 5.10 |
| N% | 15.24 | 15.27 | 15.02 |
| Cl% | 12.88 | 12.74 | 12.97 |

EXAMPLE 12

N-[(2',4'-diamino) phenyl]-3-chloro benzoquinone imine, having the below formula, is prepared as follows:

To a solution, cooled by an ice-salt mixture, of 0.02 mole (2.87 g) of 3-chloro 4-amino phenol and 0.02 mole (3.62 g) of metphenylenediamine dihydrochloride in 70 cc of water to which have been added 50 cc of isopropanol, there is added 0.02 mole (4.6 g) of ammonium persulfate in 50 cc of water to which have been added 25 cc of ammonia at 22° Be. The reaction mixture is allowed to stand for 15 minutes at 0° C. The above indoaniline which has precipitated is filtered and washed with water. After recrystallization in a dimethylformamidewater mixture and vacuum drying, the product melts at 215° C.

Molecular weight calculated for $C_{12}H_{10}N_3OCl$ = 247.5

Molecular weight found by potentiometric determination is dimethylformamide with 0.1N tetra-n-butylammonium hydroxide in solution in a mixutre of isopropanol and methanol = 242

| Analysis | Calculated for | Found | |
|---|---|---|---|
| | $C_{12}H_{10}N_3OCl$ | | |
| C% | 58.18 | 57.95 | 57.87 |
| H% | 4.44 | 4.42 | 4.57 |
| N% | 16.97 | 16.62 | 16.83 |
| Cl% | 14.34 | 14.36 | 14.29 |

EXAMPLE 13

N-[(2',4'-diamino-5'-methoxy) phenyl]-3-chloro benzoquinone imine, having the below formula, is prepared as follows:

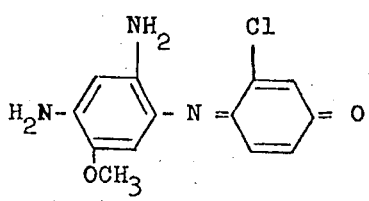

There are dissolved 0.03 mole (4.30 g) of 3-chloro-4-amino phenol and 0.03 mole of 2,4-diamino anisole dihydrochloride (6.33 g) in 250 cc of a 0.4N soda solution. To this solution, cooled to 0° C, there is added, with stirring, 0.03 mole (6.9 g) of ammonium persulfate dissolved in 100 cc of water to which have been added 20 cc of ammonia at 22° Be. The above indoaniline which precipitates almost immediately is filtered, washed with water and recrystallized in a pyridine-water mixture. After vacuum drying, it melts at 218° C.

Molecular weight calculated for $C_{13}H_{12}N_3O_2Cl$ = 277.5

Molecular weight found by potentiometric determination in acetic acid by perchloric acid = 273.

| Analysis | Calculated for | Found | |
|---|---|---|---|
| | $C_{13}H_{12}N_3O_2Cl$ | | |
| C% | 56.21 | 55.77 | 55.84 |
| H% | 4.32 | 4.44 | 4.39 |
| N% | 15.13 | 15.11 | 14.95 |

EXAMPLE 14

N-[(2'-acetylamino-4'-dimethylamino) phenyl]-3-chloro benzoquinone imine, having the below formula, is prepared as follows:

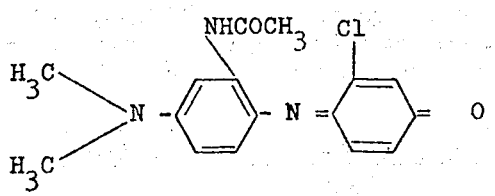

on the one

To a solution of 0.015 mole (2.67 g) of 3-acetylamino N,N-dimethylaniline in 25 cc of isopropanol, cooled in an ice-salt mixture, there are added simultaneously, with two dropping funnels, on the one hand, 0.01 mole (1.43 g) of 3-chloro-4-amino phenol in 15 cc of isopropanol, and on the other hand, 0.012 mole (2.75 g) of ammonium persulfate in 35 cc of water to which have been added 6 cc of ammonia at 22° Be. The above indoaniline which immediately precipitates in the form of green crystals is filtered, washed with water and then with a 50 percent aqueous isopropanol solution. After vacuum drying the product melts at 198° C.

Molecular weight calculated for $C_{16}H_{16}N_3O_2Cl$ = 317.5

Molecular weight found by potentiometric determination in acetic acid by perchloric acid = 322.

| Analysis | Calculated for | Found | |
|---|---|---|---|
| | $C_{16}H_{16}N_3O_2Cl$ | | |
| C% | 60.47 | 60.05 | 59.84 |
| H% | 5.04 | 5.08 | 5.12 |
| N% | 13.22 | 13.07 | 13.23 |
| Cl% | 11.18 | 11.16 | 11.07 |

EXAMPLE 15

N-[(2'-acetylamino-4'-amino-5'-methyl) phenyl]-2-chloro benzoquinone imine hydrochloride, having the below formula, is prepared as follows:

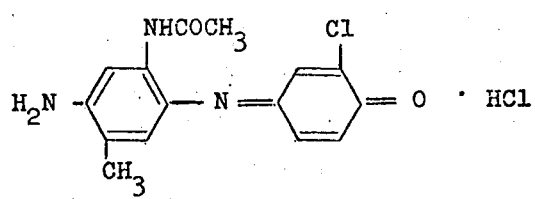

There are dissolved 0.01 mole (1.64 g) of 2-amino 4-acetylamino toluene and 0.01 mole (1.80 g) of 2-chloro 4-amino phenol hydrochloride in 50 cc of water to which have been added 10 cc of a normal HCl solution. To this resulting solution, previously cooled to 0° C, are added, little by little, with stirring, 23 cc of a 28 percent ferric chloride solution. When the addition is finished, the stirring is continued for 10 minutes. The above indoaniline hydrochloride precipitates and is filtered therefrom. After washing with water and with acetone and then vacuum drying, the product is chromatographically pure and melts with decomposition at 230° C.

| Analysis | Calculated for | Found | |
|---|---|---|---|
| | $C_{15}H_{14}N_3O_2Cl \cdot HCl$ | | |
| C% | 52.94 | 52.66 | 52.73 |
| H% | 4.41 | 4.50 | 4.48 |
| N% | 12.35 | 12.15 | 12.27 |
| Cl% | 9.41 | 20.68 | 20.73 |

EXAMPLE 16

N-[(3',5'-dimethyl-2',4'-diamino) phenyl]-2,3-dimethyl benzoquinone imine described in Exaample 4, is prepared in accordance with method 2 as follows:

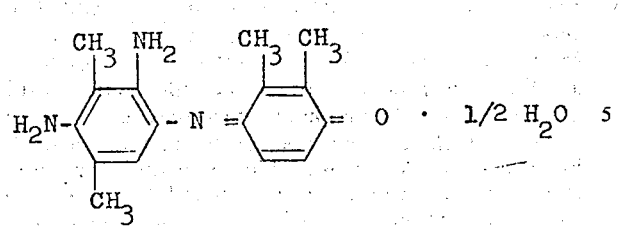

Step 1 — Preparation of 2,3-dimethyl benzoquinoneimine

There are introduced 0.05 mole (6.85 g) of 2,3-dimethyl-4-amino phenol and 0.075 mole (17.4 g) of silver oxide and 55 g of anhydrous sodium sulfate in 600 cc of anhydrous isopropyl ether. The resulting mixture is heated for four hours with reflux and stirring. The reaction mass is then filtered and the filtrate concentrated under vacuum to a volume of 10 cc. After cooling, 10 cc of ligroin are added to the concentrated filtrate to precipitate 2,3-dimethyl benzoquinone imine, which is filtered and vacuum dried. There are obtained 5.5 g of this product which melts at 80° C.

Step 2

There are dissolved 0.003 mole (0.627 g) of 1,3-dimethyl-2,4-diamino benzene dihydrochloride in 10 cc of water to which has been added 1 cc of ammonia at 22' Be. To this solution, cooled in ice, there is added 0.002 mole (0.27 g) of the above 2,3-dimethyl benzoquinone monoimine, dissolved at the moment of use in 5 cc of isopropanol. The above indoaniline, which precipitates, is filtered, washed with water and vacuum dried. The indoaniline melts at 206° C and does not show any drop in its melting point when mixed with the product prepared according to Example 4.

EXAMPLE 17

The double chloride of zinc and N-[7'(6'-hydroxy-4'-methyl-1'-oxa-4'-aza-1',2',3',4'-tetrahydro)-naphthyl]-2,5-dimethyl benzoquinoneimine having the below formula, is prepared as follows:

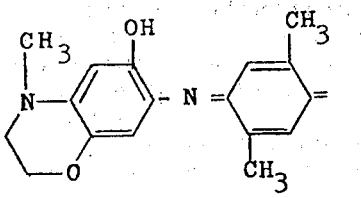

Into 15 cc of absolute ethyl alcohol there are introduced 0.01 mole (1.65 g) of 6-hydroxy-4-methyl phenomorpholine, 0.01 mole (1.51 g) of 2,5-dimethyl paranitrosophenol and 1.5 g of anhydrous zinc chloride. The reaction mixture is heated 45 minutes with reflux, with stirring. The reaction mass is then filtered hot to eliminate an insoluble light material. After cooling, 2.10 g of the double chloride of zinc and indoaniline are filtered which, after washing with alcohol anad ethyl acetate, is chromatographically pure.

EXAMPLE 18

N-[(2',4'-diamino-6'-methyl) phenyl]-2,5-dimethyl benzoquinone imine, having the below formula, is prepared as follows:

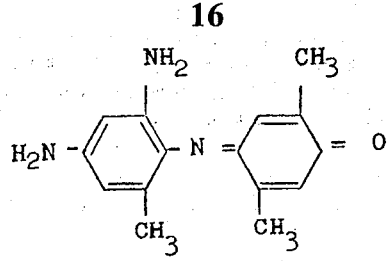

There are dissolved 0.01 mole (1.37 g) of 2,5-dimethyl-4-amino phenol and 0.01 mole (1.95 g) of 3,5-diamino toluene dihydrochloride in 80 cc of 1.5N soda solution. To this solution, cooled in ice, there is added, little by little, with stirring, 0.01 mole (2.3 g) of ammonium persulfate dissolved in 50 cc of water. When the addition is finished, the stirring is continued 10 minutes. The above indoaniline is filtered, washed with water and vacuum dried. The product is chromatographically pure and melts at 125° C.

Molecular weight calculated for $C_{15}H_{17}N_3O = 255$

Molecular weight found by potentiometric determination in methylisobutylketone by perchloric acid = 258.

EXAMPLE 19

N-[2',4'-diamino-5'-methoxy) phenyl]-2,6-dimethyl benzoquinoneimine, having the formula, is prepared as follows:

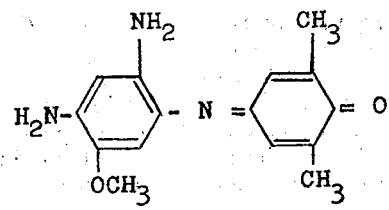

To a solution, cooled by an ice-salt mixture, of 0.01 mole (2.28 g) of ammonium persulfate in 30 cc of water there are added, first, 0.01 mole (2.11 g) of 2,4-diamino anisole dihydrochloride in 100 cc of water and then 30 cc of ammonia at 22° Be. Immediately thereafter, there is added 0.01 mole (1.91 g) of 2,6-dimethyl paraaminophenol monohydrate hydrochloride in solution in 50 cc of water. The reaction mixture immediately turns blue and and the above indoaniline rapidly crystallizes. The crude product is isolated by filtering. Its chromatogram reveals as an impurity a small amount of N-[(4'-hydroxy-3',5'-dimethyl) phenyl]-2,6-dimethyl benzoquinoneimine resulting from the oxidizing condensation of 2,6-dimethyl paraaminophenol on it. After washing in iced acetone, 0.95 g of the pure product is obtained, which melts at 146° C.

Molecular weight calculated for $C_{15}H_{17}O_2N_3 = 271$.

Molecular weight found by potentiometric determination in acetic acid by perchloric acid = 266.

| Analysis | Calculated for $C_{15}H_{17}O_2N_3$ | Found | |
|---|---|---|---|
| C% | 66.42 | 65.69 | 65.77 |
| H% | 6.27 | 6.29 | 6.31 |
| N% | 15.50 | 15.72 | 15.69 |

EXAMPLE 20

N-[(2',4'-diamino-6'-methyl) phenyl]-2,6-dimethyl benzoquiononeimine, having the below formula, is prepared as follows:

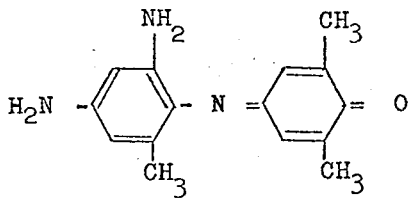

To a solution, cooled by an ice-salt mixture, of 0.06 mole (13,68 g) of ammonium persulfate in 180 cc of water there are added, first, 120 cc of ammonia at 22° Be; and then simultaneously, with two dropping funnels, on the one hand, 0.06 mole (11.7 g) of 3,5-diamino toluene dihydrochloride in 260 cc of water and on the other hand, 0.06 mole (11.46 g) of 2,6-dimethyl paraaminophenol monohydrate hydrochloride in 600 cc of water. The reaction mixture rapidly takes on a blue coloring and the above indoaniline crystallizes after some minutes. It is isolated by filtering and thereafter washed with water and then with a little iced acetone to eliminate traces of N-[(4'-hydroxy-3',-5'-dimethyl) phenyl]-2,6-dimethyl benzoquinoneimine. The resulting product is chromatographically pure and melts at 171°.

Molecular weight calculated for $C_{15}H_{17}ON_3$= 255.

Molecular weight found by potentiometric determination in methylisobutylketone by perchloric acid = 256

| Analysis | Calculated for | Found | |
|---|---|---|---|
| | $C_{15}H_{17}O\ N_3$ | | |
| C% | 70.59 | 69.82 | 69.73 |
| H% | 6.66 | 6.79 | 6.89 |
| N% | 16.47 | 16.28 | 16.46 |

EXAMPLE 21

N-[(2',4'-diamino-5'-methyl) phenyl]-2,6-dimethyl benzoquinoneimine, having the below formula, is prepared as follows:

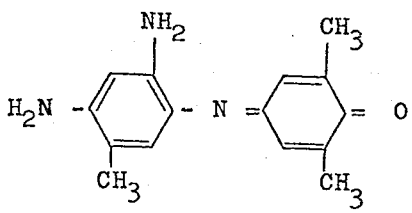

To a solution, cooled by an ice-salt mixture, of 0.02 mole (4.56 g) of ammonium persulfate in 60 cc of water and 40 cc of ammonia at 22° Be, there are added simultaneously, with two dropping funnels, on the one hand, 0.02 mole (3.83 g) of 2,6-dimethyl paraminophenol monohydrate hydrochloride in solution in 200 cc of water and, on the other hand, 0.02 mole (2.44 g) of metatoluylenediamine solution in 25 cc of acetone. The reaction mixture rapidly takes on a blue shade and the above indoaniline crystallizes. It is isolated by filtering, washed with water and vacuum dried. The product is chromatographically pure and melts at 113° C.

Molecular weight calculated for $C_{15}H_{17}O\ N_3$= 255.

Molecular weight found by potentiometric determination in methylisobutylketone by perchloric acid = 260.

| Analysis | Calculated for | Found | |
|---|---|---|---|
| | $C_{15}H_{17}O\ N_3$ | | |
| C% | 70.59 | 70.33 | 70.27 |
| H% | 6.66 | 6.79 | 6.81 |
| N% | 16.47 | 16.22 | 16.24 |

EXAMPLE 22

N-[(2',4'-diamino-3',5'-dimethyl) phenyl-2,6-dimethyl benzoquinoneimine, having the below formula, is prepared in accordance with method 1 as follows:

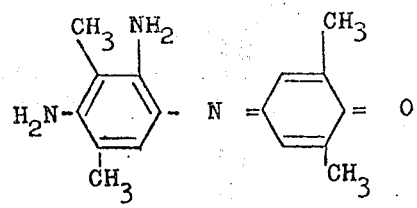

To a solution, cooled with an ice-salt mixture, of 0.04 mole (9.12 g) of ammonium persulfate in 120 cc of water and 80 cc of ammonia at 22° Be, there are added simultaneously and rapidly, with two dropping funnels, on the one hand, 0.04 mole (7.66 g) of 2,6-dimethyl paraaminophenol monohydrate hydrochloride in solution in 400 cc of water and, on the other hand, 0.04 mole (8.36 g) of 1,3-dimethyl-2,4-diamino benzene dihydrochloride in solution in 200 cc of water. The reaction mixture immediately turns blue and the above indoaniline crystallizes. The crystallized product is filtered, washed with ice water and then with iced acetone and vacuum dried 3.6 g of chromatographically pure product is obtained which melts at 196°.

Molecular weight calculated for $C_{16}H_{19}O\ N_3$= 269.

Molecular weight found by potentiometric determination in acetric acid by perchloride acid = 269.

| Analysis | Calculated for | Found | |
|---|---|---|---|
| | $C_{16}H_{19}O\ N_3$ | | |
| C% | 71.37 | 70.46 | 70.68 |
| H% | 7.06 | 7.05 | 7.03 |
| N% | 15.61 | 15.48 | 15.37 |

EXAMPLE 23

N-[(2',4'-diamino-3',5'-dimethyl) phenyl]-2-methyl benzoquinoneimine, having the below formula, is prepared as follows:

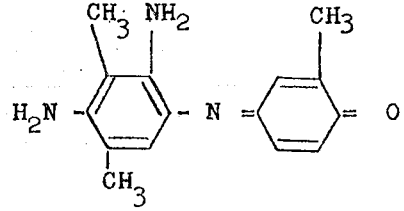

To a solution of 0.04 mole (6.38 g) of 2-methyl paraaminophenol hydrochloride and 0.04 mole (8.36 g) of 1,3-dimethyl-2,4-diamino benzene dihydrochloride in 320 cc of a 0.4 N soda solution there is added, with stirring, 0.04 mole (9.12 g) of ammonium persulfate in 120 cc of water, while cooling the reaction mixture with an ice-salt. The above indoaniline crystallizes immediately. The crystallized product is filtered and washed with water. After recrystallization in an acetonewater mixture, it melts at 123°.

Molecular weight calculated for $C_{15}H_{17}O\ N_3 = 255$.

Molecular weight found by potentiometric determination in acetic acid by perchloride acid = 249.

| Analysis | Calculated for | Found | |
|---|---|---|---|
| | $C_{15}H_{17}O\ N_3$ | | |
| C% | 70.59 | 70.07 | 69.88 |
| H% | 6.66 | 6.60 | 6.80 |
| N% | 16.47 | 16.46 | 16.22 |

EXAMPLE 24

N-[(4'-dimethylamino-2'-amino) phenyl]-2,6-dimethyl benzoquinoneimine, having the formula below, is prepared as follows:

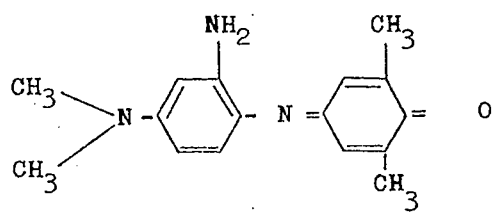

To a solution, cooled by an ice-salt mixture, of 0.02 mole (4.6 g) of ammonium persulfate in 60 cc of water and 50 cc of ammonia at 22° Be, there are added simultaneously and rapidly, with two dropping funnels, on the one hand, 0.02 mole (3,83 g) of 2,6l-dimethyl paraaminophenol monohydrate hydrochloride in 200 cc of water and, on the other hand, 0.02 mole (4.18 g) of N,N-dimethylmetaphenylenediamine dihydrochloride in 100 cc of water. The reaction mixture instantly turns blue and the above indoaniline precipitates in crystallized form. The crude product is filtered, washed with water and then with iced acetone to eliminate traces of N-[(4'-hydroxy-3', 5'-dimethyl) phenyl]-2,6-dimethyl benzoquinoneimine. After recrystallization in a pyridinewater mixture and vacuum drying, the product melts at 240°.

Molecular weight calculated for $C_{16}H_{19}N_3O = 269$.

Molecular weight found by potentiometric determination in acetic acid by perchloric acid = 264.

| Analysis | Calculated for | Found | |
|---|---|---|---|
| | $C_{16}H_{19}N_3O$ | | |
| C% | 71.38 | 71.76 | 71.62 |
| H% | 7.06 | 7.14 | 7.12 |
| N% | 15.62 | 15.61 | 15.56 |

EXAMPLE 25

The double chloride of zinc and N[7'-(6'-hydroxy-4'-methyl-1'-oxa-4'-aza-1', 2', 3', 4'-tetrahydro)-naphthyl]-2,6-dimethyl benzoquinoneimine having the below formula, is prepared as follows:

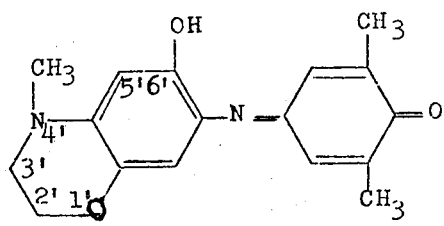

In 12 cc of absolute ethyl alcohol, to which have been added two drops of hydrochloric acid (d= 1:18) there are introduced 0.01 mole (1.65 g) of 6-hydroxy-4-methyl phenomorpholine, 0.01 mole (1.51 g) of 2,6-dimethyl paranitrosophenol and 1.5 g of anhydrous zinc chloride. The reaction mixture is heated for 30 minutes with reflux. After cooling, there are filtered therefrom, in the form of green crystals, 1.9 g of double chloride of zinc and the above indoaniline which, after washing with 50° ethyl alcohol, is chromatographically pure.

EXAMPLE 26

N-[7'-(6'-hydroxy-1'-oxa-4'-aza 1',2', 3', 4'-tetrahydro)-naphthyl]-2-methyl benzoquinoneimine monohydrate, having the below formula, is prepared as follows:

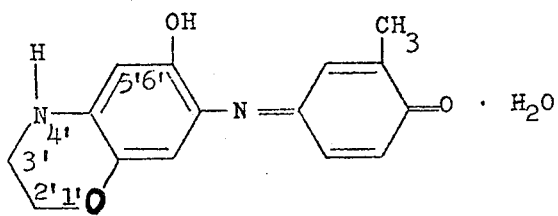

There are dissolved 0.004 mole (0.064 g) of 6-hydroxy phenomorpholine and 0.004 mole (0.637 g) of 2-methyl-4-amino phenol hydrochloride in 400 cc of 0.025 N soda solution. Air is bubbled for three hours into the reaction mixture which progressively takes on a green coloring 0.460 g of crystallized indoaniline is filtered which, after washing with water and vacuum drying, melts at 298°.

| Analysis | Calculated for | Found | |
|---|---|---|---|
| | $C_{15}H_{14}O_3N_2\ H_2O$ | | |
| C% | 62.50 | 62.23 | 62.32 |
| H% | 5.56 | 5.75 | 5.64 |
| N% | 9.72 | 9.80 | 9.95 |

EXAMPLE 27

N-[(2',4'-diamino) phenyl]-2,6-dimethyl-benzoquinoneimine, having the formula below, is prepared as follows:

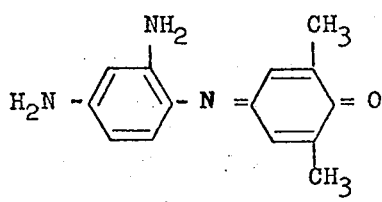

To a solution of 0.04 mole (9.12 g) of ammonium persulfate in 120 cc of water, to which have been added 120 cc of ammonia at 22° Be, which solution previously has been cooled in an ice-salt mixture, there are added rapidly and simultaneously, with two dropping funnels, on the one hand, 0.04 mole (7.66 g) of 2,6-dimethyl paraaminophenol monohydrate monohydrochloride in 200 cc of water, and on the other hand, 0.04 mole (7.24 g) of metaphenylenediamine dihydrochloride. The reaction mixture immediately takes on a blue coloring and the above indoaniline precipitates in crystallized form. It is filtered, washed with water and then with acetone. After vacuum drying, the product melts at 162°.

Molecular weight calculated for $C_{14}H_{15}N_3O = 241$.
Molecular weight found by potentiometric determination in acetic acid by perchloric acid = 243.

| Analysis | Calculated for | Found | |
|---|---|---|---|
| | $C_{14}H_{15}O N_3$ | | |
| C% | 69.68 | 69.34 | 69.22 |
| H% | 6.27 | 6.29 | 6.36 |
| N% | 17.41 | 17.11 | 17.21 |

EXAMPLE 28

N-[(4'-N,N-dimethylamino-2'-acetylamino) phenyl]-2,6-dimethyl benzoquinoneimine, having the below formula, is prepared as follows:

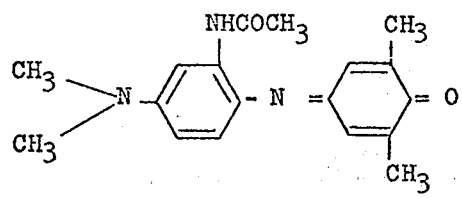

There are dissolved, on the one hand, 0.01 mole (1.91 g) of 2,6-dimethyl paraaminophenol monohydrate hydrochloride and on the other hand, 0.0125 mole (2.22 g) of N,N-3-dimethylamino acetanilide in 100 cc of water, 20 cc of isopropanol and 5 cc of ammonia at 22° Be. To this resulting solution, cooled with an ice-salt mixture, there is added little by little, with stirring, 0.02 mole of potassium ferricyanide in solution in 30 cc of water. When the addition is finished, stirring is continued for 30 minutes. 300 cc of ice water is then added to the reaction mixture. 1.15 g of the above indoaniline are recovered by filtration. After washing with water and acetone, the product is chromatographically pure and melts at 237°.

Molecular weight calculated for $C_{18}H_{21}O_2N_3 = 311$.
Molecular weight found by potentiometric determination in acetic acid by perchloric acid = 304.

EXAMPLE 29

N-[(2',4'-diamino-5'-methoxy) phenyl]-2-methyl benzoquinonemine, having the below formula, is prepared as follows:

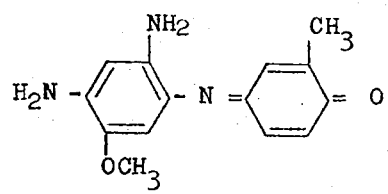

There is dissolved 0.05 mole (6.15 g) of 2-methyl 4-amino phenol in 100 cc of 0.5 N soda solution. To this solution there are added 0.05 mole (11.4 g) of ammonium persulfate in 150 cc of water, to which have been added 15 cc of ammonia at 22° Be and 0.05 mole (10.55 g) of 2,4-diamino anisole dihydrochloride in solution in 250 cc of water to which have been added 5 cc of ammonia at 22° Be, while keeping the temperature of the reaction mixture in the vicinity of 0° C. The above indoaniline precipitates in crystallized form. It is filtered, washed with water and vacuum dried. The product is chromatographically pure and melts at 155°.

| Analysis | Calculated for | Found | |
|---|---|---|---|
| | $C_{14}H_{15}O_2N_3$ | | |
| C% | 65.37 | 65.19 | 65.03 |
| H% | 5.83 | 5.85 | 6.00 |
| N% | 16.33 | 16.35 | 16.22 |

EXAMPLE 30

N-[(6'-amino-1'-oxa-4'-aza-1',2',3',4'tetrahydro)-7'-naphthyl]-2-methyl benzoquinoneimine, having the below formula, is prepared as follows:

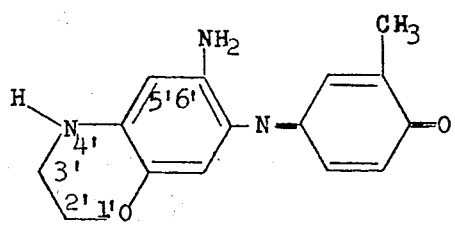

0.02 mole (3.19 g) of 2-methyl 4-amino phenol hydrochloride and 0.02 mole (4.46 g) of 6-amino phenomorpholine are dissolved in 280 cc of 0.25 N soda solution. Air is bubbled in this solution for three hours. Then acetic acid is added to the reaction mixture until a pH equal to 8.5 is obtained. The above indoaniline which precipitates is filtered in crystallized form. After washing with water and vacuum drying, the product is chromatographically pure and melts at 288°.

Molecular weight calculated for $C_{15}H_{15}O_2N_3 = 269$.
Molecular weight found by potentiometric determination in acetic acid by perchloric acid = 264.

| Analysis | Calculated for | Found | |
|---|---|---|---|
| | $C_{15}H_{15}O_2N_3$ | | |
| C% | 66.91 | 66.41 | 66.28 |
| H% | 5.59 | 5.56 | 5.48 |
| N% | 15.61 | 15.54 | 15.66 |

EXAMPLE 31

N-[(2',4'-diamino-3',5'-dimethyl) phenyl]-2,6-dimethyl benzoquinoneimine, having the below formula, is prepared in accordance with method 2 as follows:

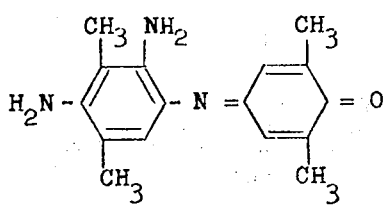

0.003 mole (0.627 g) of 1,3-dimethyl 2,4-diamino benzene dihydrochloride is dissolved in 11 cc of 0.82 N soda solution. To this solution, cooled to 0°, there is added 0.002 mole (0.339 g) of 2,6-dimethyl N-chlorobenzoquinone monoimine in solution in 6 cc of isopropanol. The reaction mixture rapidly turns blue. It is allowed to stand for one hour at 0.20. Then 0.400 g of the above indoaniline is isolated in the form of beautiful green flakes with golden glints by filtering. After washing with water and extended vacuum drying, the product melts at 196° (no drop of melting point is observed when used in mixture with the product prepared according to Example 22).

Molecular weight calculated for $C_{16}H_{19}O\ N_3 = 269$
Molecular weight found by potentiometric determination in acetic acid by perchloric acid = 272.

EXAMPLE 32

N-[2',4'-diamino-3',5'-dimethyl) phenyl]-2,6-dimethyl benzoquinoneimine, having the below formula, is prepared in accordance with method 3 as follows:

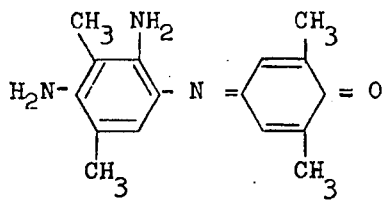

0.003 mole (0.627 g) of 1,3-dimethyl 2,4-diamino benzene dihydrochloride is dissolved in 10 cc of water to which has been added 1 cc of ammonia at 22° Be. To this solution, cooled to 0° C, there is added 0.003 mole (0.405 g) of 2,6-dimethyl benzoquinone monoimine in 5 cc of isopropanol. The reaction mixture immediately takes on a blue coloring and the above indoaniline precipitates in a few seconds in the form of green-mordore crystals. The indoaniline is filtered, washed with distilled water and vacuum dried. There is obtained 0.24 g of chromatographically pure product, which melts at 196° (no drop in melting point when used with the product prepared according to Example 22 is observed).

Molecular weight calculated for $C_{16}H_{19}O\ N_3 = 269$.
Molecular weight found by potentiometric determination in acetic acid by perchloric acid = 268.

EXAMPLE 33

The following hair-setting lotion composition is prepared:

| | |
|---|---|
| Dye of Example 1 | 0.05 g |
| Vinyl acetate-crotonic acid copolymer (vinyl acetate 90%, crotonic acid 10% molecular weight, 45,000 – 50,000) | 2 g |
| Ethyl alcohol, 96° titer, q.s.p. for 50° | |
| Water, q.s.p. | 100 g |
| Triethanolamine, q.s.p. pH 7 | |

This hair-setting lotion composition when applied to bleached hair, imparts thereto a parme shade with pearly glints

EXAMPLE 34

The following hair-setting lotion composition is prepared:

| | |
|---|---|
| Dye of Example 2 | 0.025 g |
| Vinyl acetate-crotonic acid copolymer (vinyl acetate 90%, crotonic acid 10%, molecular weight, 45,000 – 50,000) | 2 g |
| Ethyl alcohol, 96° titer, q.s.p. 50° | |
| Water, q.s.p. | 100 g |
| Ammonia, at 22° Be, q.s.p. pH 6 | |

This hair-setting lotion when applied to bleached hair, imparts thereto a pearly pale mauve shade.

EXAMPLE 35

The following dye composition is prepared:

| | |
|---|---|
| Dye of Example 2 | 0.10 g |
| Ethyl alcohol, 96° titer, q.s.p. 60° | |
| Water, q.s.p. | 100 g |
| The final pH of the solution is 8.5 | |

This dye composition when applied for 20 minutes, at ambient temperature, to 95% white hair, imparts thereto, after rinsing the shampooing, a mauve shade.

EXAMPLE 36

The following dye composition is prepared:

| | |
|---|---|
| Dye of Example 3 | 0.4 g |
| Ethyl alcohol, 96° titer | 40 g |
| Water, q.s.p. | 100 g |
| 1% lactic acid, q.s.p. pH 5 | |

This dye composition when applied to 95% naturally white hair for 20 minutes at ambient temperature, imparts thereto after rinsing and shampooing an ash beige color with violet glints.

EXAMPLE 37

The following dye composition solution is prepared:

| | |
|---|---|
| Dye of Example 4 | 0.2 g |
| Butylglycol | 5 g |
| Lauryl alcohol, oxyethylenated with 10.5 moles of ethylene oxide | 5 g |
| Water, q.s.p. | 100 g |

The final pH of the dye composition is 5.5.

This dye composition when applied to 95% naturally white hair for 20 minutes at ambient temperature, imparts thereto after rinsing and shampooing, a very luminous intense violet shade.

EXAMPLE 38

The following hair-setting lotion composition is prepared:

| | |
|---|---|
| Dye of Example 5 | 0.005 g |
| Vinyl acetate-crotonic acid copolymer (vinyl acetate, 90% — crotonic acid, 10%, molecular weight 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto a pearly appearance with almond green glints.

EXAMPLE 39

The following hair-setting lotion is prepared:

| | |
|---|---|
| Dye of Example 5 | 0.025 g |
| N-[(4'-hydroxy)phenyl]-2,6-dimethyl benzoquinone imine | 0.025 g |
| Vinyl acetate-crotonic acid copolymer (vinyl acetate, 90% — crotonic acid 10%, molecular weight 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto a silvery gray shade with iridescent glints.

EXAMPLE 40

The following hair-setting lotion composition is prepared:

| | |
|---|---|
| Dye of Example 6 | 0.025 g |
| Vinyl acetate-crotonic acid copolymer (vinyl acetate - 90%, crotonic acid- 10%, molecular weight 45,000 – 50,000) | 2 g |
| Ethyl alcohol, 96° titer, q.s.p. 50° | |
| Water, q.s.p. | 100 g |
| Ammonia, 22° Be, q.s.p. pH 8 | |

This hair-setting lotion when applied to bleached hair, imparts thereto a silvery pale mauve shade.

EXAMPLE 41

The following hair-setting lotion is prepared:

| | |
|---|---|
| Dye of Example 6 | 0.05 g |
| N-[(2',4'-diamino-5'-methoxy)phenyl] benzoquinoneimine | 0.025 g |
| Vinyl acetate-crotonic acid copolymer (vinyl acetate - 90%, crotonic acid- 10%, molecular weight 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto a silvery blue gray shade.

EXAMPLE 42

The following hair-setting lotion is prepared:

| | |
|---|---|
| Dye of Example 8 | 0.1 g |
| Vinyl acetate-crotonic acid copolymer (vinyl acetate - 90%, crotonic acid- 10%, molecular weight 45,000 to 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair imparts thereto an intense gray blue shade.

EXAMPLE 43

The following hair-setting lotion is prepared:

| | |
|---|---|
| Dye of Example 9 | 0.05 g |
| Vinyl acetate-crotonic acid copolymer (vinyl (acetate - 90%, crotonic acid - 10%, molecular weight 45,000 to 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion whnn applied to bleached hair, imparts thereto a pearly ash beige shade.

EXAMPLE 44

The following dye composition is prepared:

| | |
|---|---|
| Dye of Example 9 | 0.05 g |
| Butylglycol | 5 g |
| Lauryl alcohol oxyethylenated with 10.5 moles of ethylene oxide | 5 g |
| Water, q.s.p. | 100 g |
| Ammonia, at 22° Be, q.s.p. pH 8.5 | |

This dye composition when applied to 95% naturally white hair, for 15 minutes at ambient temperature, imparts thereto, after rinsing and shampooing, a coppery blond shade.

EXAMPLE 45

The following hair-setting lotion is prepared:

| | |
|---|---|
| Dye of Example 10 | 0.10 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water q.s.p. | 100 g |
| Ammonia, at 22° Be, q.s.p. pH 8 | |

This hair-setting lotion when applied to bleached hair, imparts thereto a silvery mauve gray shade.

EXAMPLE 46

The following dye composition is prepared:

| | |
|---|---|
| Dye of Example 11 | 0.1 g |
| Ethyl alcohol, 96° titer | 20 g |
| Water, q.s.p. | 100 g |
| Ammonia, at 22° Be, q.s.p. pH 10 | |

This dye composition when applied to 95% naturally white hair for 20 minutes at ambient temperature, imparts, after rinsing and shampooing, a silvery gray shade.

EXAMPLE 47

The following hair-setting lotion is prepared:

| | |
|---|---|
| Dye of Example 12 | 0.025 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto a pearly appearance with mauve glints.

EXAMPLE 48

The following hair-setting lotion is prepared:

| | |
|---|---|
| Dye of Example 13 | 0.05 g |
| Vinyl acetate-crotonic acid copolymer (vinyl acetate - 90%, crotonic acid - 10%, molecular weight, 45,000 – 50,000) | 1 g |
| Ethyl alcohol, 96° titer, q.s.p. 25° | |
| Water, q.s.p. | 100 g |
| 1% lactic acid solution, q.s.p. pH 5 | |

This hair-setting lotion when applied to bleached hair, imparts thereto an intense pearly pink shade.

EXAMPLE 49

The following dye composition is prepared:

| | |
|---|---|
| Dye of Example 14 | 0.2 g |
| Ethyl alcohol, 96° titer, q.s.p. 65° | |
| Water, q.s.p. | 100 g |
| 1% lactic acid, q.s.p. pH 5.5 | |

This dye composition when applied to 95% naturally white hair for 25 minutes at 35°, imparts thereto after rinsing and shampooing a light pearly green shade.

EXAMPLE 50

The following dye composition is prepared:

| | |
|---|---|
| Dye of Example 13 | 0.2 g |
| Ethyl alcohol, 96° titer, q.s.p. 50° | |
| Water, q.s.p. | 100 g |
| Ammonia, at 22° Be, q.s.p. pH 10 | |

This dye composition when applied to 95% naturally white hair for 20 minutes at ambient temperature, imparts thereto after rinsing and shampooing, a luminous beige with light pink glints.

EXAMPLE 51

The following hair-setting lotion is prepared:

| | |
|---|---|
| Dye of Example 15 | 0.05 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 5.5 | |

This hair-setting lotion when applied to bleached hair imparts thereto, a very luminous, pearly blue green shade.

EXAMPLE 52

The following dye composition is prepared:

| | |
|---|---|
| Dye of Example 11 | 0.1 g |
| N-[(4'-hydroxy-3',5'-dimethyl) phenyl]-2,6-dimethyl benzoquinone imine | 0.1 g |
| Ethyl alcohol, 96° titer | 30 g |
| Water, q.s.p. | 100 g |
| Ammonia, at 22° Be, q.s.p. pH 10 | |

This dye composition when applied to bleached hair for 10 minutes at ambient temperature, imparts thereto, after rinsing and shampooing, a silvery gray shade with rose glints.

EXAMPLE 53

The following hair-setting lotion is prepared:

| | |
|---|---|
| Dye of Example 18 | 0.05 g |
| Vinyl acetate-crotonic acid copolymer (vinyl acetate - 90%, crotonic acid - 10%, molecular weight, 45,000 to 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair imparts thereto, a bluish silvery gray shade.

EXAMPLE 54

The following hair-setting lotion is prepared:

| | |
|---|---|
| Dye of Example 17 | 0.05 g |
| Vinyl acetate - crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto a light rose beige shade with silvery glints.

EXAMPLE 55

The following dye composition is prepared:

| | |
|---|---|
| Dye of Example 16 | 0.1 g |
| Nitroparaphenylenediamine | 0.1 g |
| Butylglycol | 5 g |
| Lauryl alcohol oxyethylenated with 10.5 moles of ethylene oxide | 5 g |
| Water, q.s.p. | 100 g |
| Ammonia, at 22° Be, q.s.p. pH 6 | |

This dye composition when applied to 95% naturally white hair, for 10 minutes at ambient temperature, imparts thereto after rinsing and shampooing, a violet coloring.

EXAMPLE 56

The following hair-setting lotion is prepared:

| | |
|---|---|
| Dye according to Example 19 | 0.1 g |
| Vinyl acetate-crotonic acid copolymer (vinyl acetate - 90%, crotonic acid - 10%, average molecular weight, 45,000 - 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto a pearly rose beige shade.

EXAMPLE 57

The following dye composition is prepared:

| | |
|---|---|
| Dye according to Example 19 | 0.4 g |
| Ethyl alcohol, 96° titer | 40 g |
| Water, q.s.p. | 100 g |
| Ammonia, at 22° Be, q.s.p. pH 10 | |

This dye composition when applied to 95% naturally white hair for 20 minutes at ambient temperature, imparts thereto after rinsing and shampooing, a silvery gray shade with rose glints.

EXAMPLE 58

The following hair-setting lotion is prepared:

| | |
|---|---|
| Dye according to Example 20 | 0.02 g |
| Vinyl acetate-crotonic acid copolymer (vinyl acetate - 90%, crotonic acid - 10%, average molecular weight 45,000 - 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto a pearly pale green shade.

EXAMPLE 59

The following dye composition is prepared:

| | |
|---|---|
| Dye according to Example 21 | 0.3 g |
| Butylglycol | 5 g |
| Lauryl alcohol oxyethylenated with 10.5 moles ethylene oxide | 5 g |
| Water, q.s.p. | 100 g |

The pH is equal to 7.

This dye composition when applied to 95% naturally white hair for 15 minutes at ambient temperature, imparts thereto, after rinsing and shampooing, a silvery gray shade with violet glints.

EXAMPLE 60

The following dye composition is prepared:

| | |
|---|---|
| Dye according to Example 23 | 0.25 g |
| Butylglycol | 5 g |
| Lauryl alcohol oxyethylenated with 10.5 moles of ethylene oxide | 5 g |
| Water, q.s.p. | 100 g |

The pH is equal to 7.

This dye composition when applied to 60% naturally white hair, for 20 minutes at ambient temperature, imparts thereto, after rinsing and shampooing, a deep purplish violet shade.

EXAMPLE 61

The following hair-setting lotion is prepared:

| | |
|---|---|
| Dye of Example 23 | 0.1 g |
| Vinyl acetate-crotonic acid copolymer (vinyl acetate - 90%, crotonic acid - 10%, molecular weight, 45,000 - 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a very luminous mauve shade.

EXAMPLE 62

The following dye composition is prepared:

| | |
|---|---|
| Dye of Example 23 | 0.05 g |
| Ethyl alcohol, 96° titer | 20 g |
| Water, q.s.p. | 100 g |
| Ammonia, at 22° Be, q.s.p. pH 10 | |

This dye composition when applied to 95% naturally white hair, for 10 minutes at ambient temperature, imparts thereto, after rinsing and shampooing, a pearly violet beige shade.

EXAMPLE 63

The following dye composition is prepared:

| | |
|---|---|
| Dye of Example 23 | 0.05 g |
| Ethyl alcohol, 96° titer | 20 g |
| Water, q.s.p. | 100 g |
| 10% lactic acid, q.s.p. pH 4.5 | |

This dye composition when applied to 95% naturally white hair, for 10 minutes at ambient temperature, imparts thereto, after rinsing and shampooing, a pearly rose beige shade.

EXAMPLE 64

The following dye composition is prepared:

| | |
|---|---|
| Dye of Example 23 | 0.0025 g |
| Water, q.s.p. | 100 g |
| Ammonia at 10%, q.s.p. pH 10 | |

This dye composition when applied to bleached hair for 10 minutes at ambient temperature, imparts thereto, after rinsing and shampooing, a very luminous pale rose blond shade.

EXAMPLE 65

The following hair-setting lotion is prepared:

| | |
|---|---|
| Dye of Example 25 | 0.05 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a rose shade with golden glints.

EXAMPLE 66

The following dye composition is prepared:

| | |
|---|---|
| Dye of Example 25 | 0.4 g |
| Butylglycol | 5 g |
| Lauryl alcohol oxyethylenated with 10.5 moles of ethylene oxide | 5 g |
| Water, q.s.p. | 100 g |

The pH is equal to 7.

This dye composition when applied to 95% white hair, for 20 minutes at ambient temperature, imparts thereto, after rinsing and shampooing, a very luminous golden blond shade with rose glints.

EXAMPLE 67

The following hair-setting lotion is prepared:

| | |
|---|---|
| Dye of Example 26 | 0.15 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a pearly pale almond green shade.

EXAMPLE 68

The following hair-setting lotion is prepared:

| | |
|---|---|
| Dye of Example 29 | 0.05 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a rose shade with golden glints.

EXAMPLE 69

The following hair-setting lotion is prepared:

| | |
|---|---|
| Dye of Example 29 | 0.005 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair imparts thereto, a light blond shade that is slightly rose.

EXAMPLE 70

The following hair-setting lotion is prepared:

| | |
|---|---|
| Dye of Example 30 | 0.05 g |
| Crotonic acid-vinyl acetate copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair imparts thereto, a violet rose shade.

EXAMPLE 71

The following hair-setting lotion is prepared:

| | |
|---|---|
| Dye of Example 28 | 0.15 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a strongly silvered, pale blue shade.

EXAMPLE 72

The following dye composition is prepared:

| | |
|---|---|
| Dye of Example 22 | 0.05 g |
| Ethyl alcohol, 96° titer | 25 g |
| Water, q.s.p. | 100 g |

The pH of the dye composition is equal to 7.

This dye composition when applied to bleached hair imparts thereto, after a 15 minute contact period and after rinsing and shampooing, a slightly mauve silvery gray shade.

EXAMPLE 73

The following dye composition is prepared:

| | |
|---|---|
| Dye of Example 22 | 0.1 g |
| Ethyl alcohol, 96° titer | 20 g |
| Water, q.s.p. | 100 g |
| 10% lactic acid, q.s.p. pH 5 | |

This dye composition when applied to 95% naturally white hair, imparts thereto, after a 10 minute contact period and after rinsing and shampooing, a pearly beige gray shade.

EXAMPLE 74

The following hair-setting lotion is prepared:

| | |
|---|---|
| Dye of Example 27 | 0.03 g |
| Vinyl acetate-crotonic acid copolymer (vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a very luminous green blue shade.

EXAMPLE 75

The following hair-setting lotion is prepared:

| | |
|---|---|
| Dye of Example 24 | 0.05 g |
| Vinyl acetate-crotonic acid copolymer (as in Example 74) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a pearly green blue shade.

EXAMPLE 76

The following dye composition is prepared:

| | |
|---|---|
| Dye of Example 29 | 0.15 g |
| Ethyl alcohol, 96° titer, q.s.p. 50° | |
| Water, q.s.p. | 100 g |
| Ammonia, at 22° Be, q.s.p. pH 10 | |

This dye composition when applied for 20 minutes to 95% naturally white hair, imparts thereto, after rinsing and shampooing a violet shade.

EXAMPLE 77

The following dye composition is prepared:

| | |
|---|---|
| Dye of Example 19 | 0.2 g |
| N-[(4'-hydroxy) phenyl]-2,6-dimethyl benzoquinone imine | 0.1 g |
| Ethyl alcohol, 96° titer | 25 g |
| Water, q.s.p. | 100 g |
| Ammonia, at 22° Be, q.s.p. pH 10 | |

This dye composition when applied for 20 minutes to 95% naturally white hair, imparts thereto, after rinsing and shampooing, an ash dark gray shade with violet glints.

EXAMPLE 78

The following dye composition is prepared:

| | |
|---|---|
| Dye of Example 21 | 0.125 g |
| Nitro orthophenylenediamine | 0.10 g |
| Ethyl alcohol, 96° titer | 40 g |
| Water, q.s.p. | 100 g |
| Ammonia, at 22° Be, q.s.p. pH 9 | |

This dye composition when applied for 15 minutes to 95% naturally white hair, imparts thereto, after rinsing and shampooing, a golden green shade.

EXAMPLE 79

The following hair-setting lotion is prepared:

| | |
|---|---|
| Dye of Example 25 | 0.05 g |
| N-[(4'-dimethylamino) phenyl]-2,5-dimethyl benzoquinone imine | 0.05 g |
| Vinyl acetate-crotonic acid copolymer vinyl acetate - 90%, crotonic acid - 10%, molecular weight, 45,000 – 50,000) | 2 g |
| Ethyl alcohol, 96° titer, q.s.p. 50° | |
| Water, q.s.p. | 100 g |
| Triethanolamine, q.s.p. pH 7 | |

This hair-setting lotion when applied to bleached hair, imparts thereto, a silvery mauve shade.

What is claimed is:

1. An indoaniline having the formula

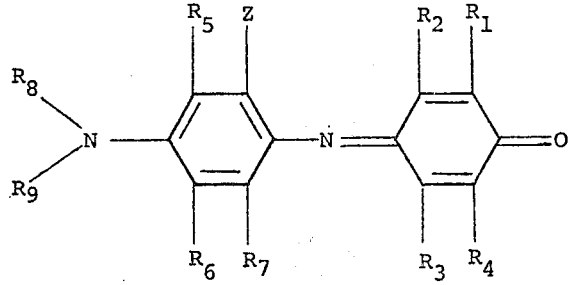

wherein $R_1$, $R_2$, $R_3$ and $R_4$ each independently represent a member selected from the group consisting of hydrogen, lower alkyl having 1–6 carbon atoms and halogen with the proviso that 1–2 of $R_1$, $R_2$, $R_3$ and $R_4$ and other than hydrogen; $R_5$, $R_6$, and $R_7$ each independently represent a member selected from the group consisting of hydrogen, lower alkyl having 1–6 carbon atoms and lower alkoxy having 1–6 carbon atoms; $R_8$ represents a member selected from the group consisting of hydrogen and lower alkyl having 1–6 carbon atoms; $R_9$ represents a member selected from the group consisting of hydrogen and lower alkyl having 1–6 carbon atoms and together with $R_6$ and the nitrogen atom to which $R_9$ is attached form 1, 4-dihydro-oxazine; and Z represents a member selected from the group consisting of amino, acetylamino and hydroxy, and b. an acid salt of said indoaniline in (a).

2. The indoaniline of claim 1 selected from the group consisting of

N-[(2',4'-diamino) phenyl]-3-methyl benzoquinone imine,

N-[(2',4'-diamino-3',5'-dimethyl) phenyl]-3-methyl benzoquinone imine,

N-[(3',5'-dimethyl-2',4'-diamino) phenyl]-3,5-dimethyl benzoquinone imine,
N-[(3',5'-dimethyl-2',4'-diamino) phenyl]-2,3-dimethyl benzoquinone imine,
N-[(2',4'-diamino) phenyl]-2,5-dimethyl benzoquinone imine,
N-[(3',5'-dimethyl-2',4'-diamino) phenyl]-2,5-dimethyl benzoquinone imine,
N-[(2',4'-diamino) phenyl]-2-chloro benzoquinone imine,
N-[(2',4'-diamino-5'-methoxy) phenyl]-2-chloro benzoquinone imine, N-[(2',4'-diamino-5'-methyl) phenyl]-2-chloro benzoquinone imine,
N-[(3',5'-dimethyl-2',4'-diamino) phenyl]-2-chloro benzoquinone imine,
N-[(2',4'-diamino) phenyl]-3-chloro benzoquinone imine,
N-[(2',4'-diamino-5'-methoxy) phenyl]-3-chloro benzoquinone imine,
N-[(2'-acetylamino-4'-dimethylamino) phenyl]-3-chloro benzoquinone imine,
N-[(2'-acetylamino-4'-amino-5'-methyl) phenyl]-2-chloro benzoquinone imine hydrochloride,
N-[(2',4'-diamino-6'-methyl) phenyl]-2,5-dimethyl benzoquinone imine,
N-[(2',4'-diamino-5'-methoxy) phenyl]-2,6-dimethyl benzoquinone imine,
N-[(2',4'-diamino-6'-methyl) phenyl]-2,6-dimethyl benzoquinone imine,
N-[(2',4'-diamino-5'-methyl) phenyl]-2,6-dimethyl benzoquinone imine,
N-[(2',4'-diamino-3',5'-dimethyl) phenyl]-2,6-dimethyl benzoquinone imine,
N-[(2',4'-diamino-3',5'-dimethyl) phenyl]-2-methyl benzoquinone imine,
N-[(4'-dimethylamino-2'-amino) phenyl]-2,6-dimethyl benzoquinone imine,
N-[7'-(6'-hydroxy-1'-oxa-4'-aza-1',2',3',4'-tetrahydro) naphthyl]-2-methyl benzoquinone imine,
N-[(2',4'-diamino) phenyl]-2,6-dimethyl benzoquinone imine,
N-[(4'-N,N-dimethylamino-2'-acetylamino) phenyl]-2,6-dimethyl benzoquinone imine,
N-[(2',4'-diamino-5'-methoxy) phenyl] 2-methyl benzoquinone imine, and
N-[7'-(6'-amino-1'-oxa-4'-aza-1',2',3',4'-tetrahydro)-naphthyl]-2-methyl benzoquinone imine.

* * * * *